United States Patent [19]

Harnisch

[11] 4,260,776

[45] Apr. 7, 1981

[54] HETEROCYCLIC DYESTUFFS

[75] Inventor: Horst Harnisch, Much, Fed. Rep. of Germany

[73] Assignee: Bayer Aktiengesellschaft, Leverkusen, Fed. Rep. of Germany

[21] Appl. No.: 5,925

[22] Filed: Jan. 23, 1979

[30] Foreign Application Priority Data

Jan. 25, 1978 [DE] Fed. Rep. of Germany ....... 2803104
Oct. 13, 1978 [DE] Fed. Rep. of Germany ....... 2844606

[51] Int. Cl.³ .................. C07D 405/04; C07D 405/14; C07D 491/052; C07D 491/147
[52] U.S. Cl. .............................. 548/364; 260/239.65; 260/239.7; 260/239.8; 260/239.9; 546/66; 546/80; 546/89; 546/269; 546/274; 548/253; 548/255; 548/256; 548/261; 548/262; 548/159; 252/301.17
[58] Field of Search ............... 548/364, 253, 255, 256, 548/262, 261; 260/239.65, 239.9, 239.7, 239.8; 546/269, 274, 66, 80, 89

[56] References Cited

U.S. PATENT DOCUMENTS

| | | | |
|---|---|---|---|
| 2,965,486 | 12/1960 | Brooker et al. | 548/364 |
| 3,717,629 | 2/1973 | Maier et al. | 548/364 |
| 3,780,057 | 12/1973 | Frey | 548/364 |
| 4,144,243 | 3/1979 | Dorlars et al. | 548/256 |

*Primary Examiner*—Henry R. Jiles
*Assistant Examiner*—Natalia Harkaway
*Attorney, Agent, or Firm*—Sprung, Felfe, Horn, Lynch & Kramer

[57] ABSTRACT

Dyestuffs of the formula

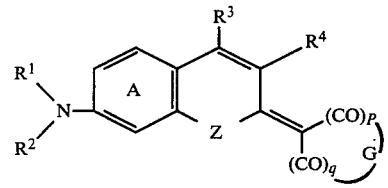

wherein
$R^1$, $R^2$, R denote H, alkyl, alkenyl, cycloalkyl, aralkyl etc.
$R^3$, $R^4$ denote H, alkyl, aralkyl, aryl, alkoxy, halogen, CN, COOH, alkoxycarbonyl, alkylsulfonyl, arylsulfonyl etc.
Z denotes O, S or —N(R)—,
p and q denote 0 or 1, but not simultaneously 0 and
G stands for the remaining members of a ring system,
with the proviso that $R_3$ is not alkyl if G is a thiazole ring, are outstanding suitable for dyeing fibre materials of all kinds in clear yellow to violet shades with good fastness properties.

3 Claims, No Drawings

HETEROCYCLIC DYESTUFFS

The invention relates to dyestuffs of the general formula

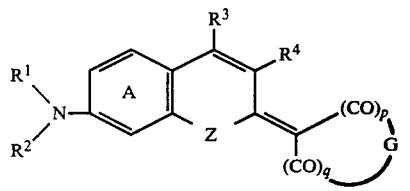

wherein $R^1$ represents hydrogen, alkyl, alkenyl, cycloalkyl, aralkyl, aryl or a 2-membered or 3-membered alkylene radical linked to the adjacent ortho-position of the ring A and $R^2$ represents hydrogen, alkyl, alkenyl, aralkyl or a 2-membered or 3-membered alkylene radical linked to the adjacent ortho-position of the ring A, or $R^1$ and $R^2$ also together represent an alkylene radical which has a total of 4 to 6 members and is optionally interrupted by NH, O or S, $R^3$ represents hydrogen, alkyl, aralkyl, aryl, alkoxy, halogen, cyano, carboxyl, alkoxycarbonyl, alkylsulphonyl or arylsulphonyl, $R^4$ represents hydrogen, alkyl, aryl, halogen, hydroxyl, alkoxy, nitro, cyano, carboxyl, alkoxycarbonyl, formyl, carbamoyl, ureido, amidino, amidinium, alkylsulphonyl, arylsulphonyl, sulpho or a heterocyclic ring system which links to a ring N atom, Z represents oxygen, sulphur or —N(R)—, R represents hydrogen, alkyl, alkenyl, aralkyl, aryl or acyl, p and q represent the numbers 0 or 1 but do not at the same time represent 0 and G represents the remaining members of a carbocyclic or heterocyclic ring system, and wherein the cyclic and acyclic radicals can carry nonionic substituents customary in dyestuff chemistry and also carboxyl and sulpho groups and can optionally be quaternised, with the proviso that $R^3$ denotes hydrogen, aryl, alkoxy, halogen, cyano, carboxyl, alkoxycarbonyl, alkylsulphonyl or arylsulphonyl if G represents the remaining members of a ring of the thiazole series.

Suitable dyestuff substituents are, for example, $C_1$-$C_4$-alkyl, OH, $C_1$-$C_4$-alkoxy, halogen, CN or $NO_2$.

Alkyl radicals $R^1$, $R^2$ and R are to be understood as meaning preferably $C_1$-$C_4$-alkyl radicals, which can be substituted by chlorine, bromine, acetyl, cyano, carboxyl, $C_1$-$C_4$-alkoxycarbonyl, carbamoyl, which is optionally substituted by 1-2 $C_1$-$C_4$-alkyl radicals, or $C_1$-$C_4$-alkoxy, acetoxy, phenoxy, sulphophenoxy, 1-2 hydroxyl or sulpho. Alkyl radicals $R^3$ and $R^4$ and those in carbamoyl radicals $R^4$ are, on the other hand, preferably unsubstituted $C_1$-$C_4$-alkyl radicals. $R^3$ can additionally denote $CF_3$.

Preferred aralkyl radicals $R^1$, $R^2$ and R are phenyl-$C_1$-$C_3$-alkyl groups, which, for example, can be substituted in the nucleus by 1-2 sulpho groups.

Suitable aryl radicals $R^1$, $R^3$, $R^4$ and R are preferably phenyl radicals, which can carry 1 to 3 further substituents, such as, for example, $C_1$-$C_4$-alkyl, $C_1$-$C_2$-alkoxy, halogen, such as chlorine and bromine, nitro, cyano, carboxyl, $C_1$-$C_4$-alkoxycarbonyl or sulpho groups.

Alkenyl groups $R^1$, $R^2$ and R preferably have 2–4 C atoms; the allyl radical is particularly preferred.

Cycloalkyl represents cyclopentyl or cyclohexyl and these can be substituted by 1–3 methyl groups.

If $R^1$ and $R^2$ together form an alkylene radical, possible radicals are, for example, —$(CH_2)_4$—, —$(CH_2)_5$—, —$(CH_2)_6$—, —$(CH_2)_2O(CH_2)_2$—, —$(CH_2)_2$—NH—$(CH_2)_2$— or —$(CH_2)_2$—S—$(CH_2)_2$.

A 2-membered or 3-membered alkylene radical $R^1$ or $R^2$ linked to the adjacent ortho-position of the ring A is preferably an ethylene or n-propylene radical which is optionally substituted by 1–3 methyl groups and/or a phenyl ring.

Acyl radicals R are, for example, $C_1$-$C_3$-alkylcarbonyl or $C_1$-$C_3$-alkylsulphonyl radicals and also $C_1$-$C_4$-alkoxycarbonyl groups.

Alkoxy groups $R^3$ and $R^4$ and those in alkoxycarbonyl groups $R^3$ and $R^4$ preferably have 1–4 C atoms. Suitable halogen radicals $R^3$ and $R^4$ are chlorine, bromine, fluorine and iodine, especially chlorine and bromine.

Akyl radicals in alkylsulphonyl radicals $R^3$ and $R^4$ preferably have 1–4 C atoms and can, for example, be substituted by chlorine or phenyl.

Suitable aryl radicals in arylsulphonyl groups $R^3$ and $R^4$ are preferably phenyl radicals, which, for example, can be monosubstituted to trisubstituted by chlorine or $C_1$-$C_4$-alkyl. Carbamoyl, ureido and amidino or amidinium radicals $R^4$ can be monosubstituted or disubstituted, preferably by $C_1$-$C_4$-alkyl, phenyl-$C_1$-$C_3$-alkyl or phenyl, and two alkyl radicals, together with the common N atom, can also form a pyrrolidine, piperidine, morpholine or piperazine ring.

Heterocyclic ring systems $R^4$ which link to a ring N atom and which may be mentioned are, in particular, 5-membered rings, such as pyrazol-1-yl, 4-chloropyrazol-1-yl, 1,2,3-triazol-1-yl, 1,2,3-triazol-2-yl, 1,2,4-triazol-1-yl, tetrazol-1-yl and also benzo-s-triazol-2-yl, and the triazoles can also contain N atoms quaternised by $C_1$-$C_4$-alkyl or benzyl.

Carbocyclic and heterocyclic ring systems, the remaining members of which are designated by G, can be monocyclic or polycyclic. They preferably consist of a 5-membered or 6-membered carbocyclic or heterocyclic ring which contains the indicated CO group or groups and to which 1–2 further carbocyclic or heterocyclic 5-membered or 6-membered rings can be fused. Examples of such ring systems which may be mentioned are those of the cyclohexane-1,3-dione, cyclohexene-1,3-dione, pyrazol-5-one (including the quaternary salts with an antipyrine-like structure), barbituric acid, thiobarbituric acid, 2,6-dioxo-2H.6H-pyridine, 2,4,6-trioxo-2H.4H.6H-pyridine, 2,4,6-trioxo-2H.4H.6H-1,3-thiazine, 2,4,6-trioxo-2H.4H.6H-1,3-oxazine, 2-aryl-4,6-dioxo-4H.6H-1,3-thiazine, 2-aryl-4,6-dioxo-4H.6H-1,3-oxazine, 2-aryl-4,6-dioxo-4H.6H-pyrimidine, 2,4-dioxo-2H.4H-pyrido[1.2-a]pyrimidine(-pyridinium), 2,4-dioxo-2H.4H-pyrimido[1.2-a]pyrimidine, 4-hydroxy-coumarin, 4-hydroxy-quinol-2-one, 1,3-diaryl-4,6-dioxo-4H.6H-pyridazine, 2,4-dioxo-2H.4H-pyrane, benzo[b]furan-2-one, benzo[b]furan-3-one, benzo[b]thien-2-one, benzo[b]thien-3-one, 3-aryl-isoxazol-5-one, indol-2-one, indol-3-one and thiazol-5-one series. Further suitable ring systems containing carbonyl groups are mentioned in the list of examples of starting components. Preferred substituents in the ring A are $C_1$-$C_3$-alkyl, chlorine and $C_1$-$C_3$-alkoxy radicals.

Preferred compounds of the formula I are those in which

R³ represents hydrogen, alkyl or aryl (in particular hydrogen),

R⁴ represents hydrogen,

Z represents oxygen and

G represents the remaining members of a radical of the indane-1,3-dione, pyrazol-5-one, barbituric acid, thiobarbituric acid, 2,6-dioxo-2H-1H-6H-pyridine, 4-hydroxycoumarin or dehydracetic acid series.

Within the scope of the invention, a preferred group of compounds corresponds to the formula

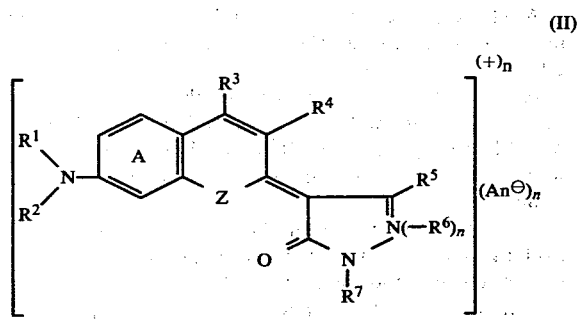

wherein $R^1$–$R^4$, A and Z possess the abovementioned meaning, $R^5$ represents hydrogen, alkyl, aralkyl, aryl, chlorine, bromine, carboxyl, alkoxycarbonyl, carbamoyl, cyano, hydroxyl, alkoxy, acyloxy or a radical of the formula —N($R^8R^9$), $R^6$ represents alkyl, alkenyl or aralkyl, n represents 0 or 1, $R^7$ represents alkyl, aralkyl, aryl or a heterocyclic radical, $R^8$ represents hydrogen, alkyl, aralkyl, cycloalkyl, aryl or a heterocyclic radical and $R^9$ represents an acyl radical, or $R^8$ and $R^9$ together with the common N atom also represent a radical

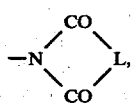

L represents 1,2-phenylene, 1,2- or 1,8-naphthylene, 1,2-cyclohexen-1-ylene, 1,2-ethenylene or 1,2-ethylene and An⁻ represents an anion, and wherein the cyclic and acyclic radicals can carry substituents customary in dyestuff chemistry.

Alkyl radicals $R^5$ preferably have 1–6 C atoms and can, for example, be substituted by halogen, such as fluorine, chlorine and bromine. Methyl and trifluoromethyl are particularly preferred.

Suitable aralkyl radicals $R^5$, $R^7$ and $R^8$ are benzyl and sulphobenzyl. Aryl radicals $R^5$ which may be mentioned are, in particular, phenyl groups, which, for example, can be substituted by 1–3 $C_1$–$C_4$-alkyl or $C_1$–$C_4$-alkoxy or 1–2 chlorine, bromine, nitro, sulpho or acylamino.

Alkoxycarbonyl radicals $R^5$ preferably contain 1–4 C atoms in the alkyl radical. Alkoxy radicals $R^5$ are preferably $C_1$–$C_4$-alkoxy groups.

Suitable acyloxy radicals $R^5$ are $C_1$–$C_4$-alkylcarbonyloxy, $C_1$–$C_2$-alkoxycarbonyloxy, phenoxycarbonyloxy, benzoyloxy, methylbenzoyloxy, chlorobenzoyloxy, methoxybenzoyloxy, phenylsulphonyloxy and toluenesulphonyloxy.

Alkyl radicals $R^6$ preferably have 1–4 C atoms and can, for example, be substituted by 1–2 hydroxyl groups or $C_1$–$C_4$-alkoxy groups.

A preferred alkenyl radical $R^6$ is the allyl group and a preferred aralkyl radical $R^6$ is the benzyl group.

Alkyl radicals $R^7$ are $C_1$–$C_4$-alkyl groups, which, for example, can be substituted by acetoxy, cyano, carbamoyl, carboxyl, $C_1$–$C_2$-alkoxycarbonyl or sulpho.

Suitable aryl radicals $R^7$ are, in addition to naphthyl, especially phenyl groups, which, for example, can be substituted by 1–3 chlorine or bromine, 1–2 methyl, $C_2$–$C_4$-alkyl, $C_1$–$C_2$-alkoxy, acylamino, nitro, cyano, carboxyl, $C_1$–$C_2$-alkoxycarbonyl, carbamoyl, $C_1$–$C_4$-alkylsulphonyl, β-sulphatoethylsulphonyl, β-acetoxyethylsulphonyl, sulphamoyl, which is optionally substituted by 1–2 $C_1$–$C_4$-alkyl, pyrrolidinosulphonyl, piperidinosulphonyl, morpholinosulphonyl, phenoxysulphonyl, sulpho and/or 6-methylbenzthiazol-2-yl.

Examples of heterocyclic radicals $R^7$ are sulpholan-3-yl and pyrimidin-2-yl. Alkyl radicals $R^8$ preferably possess 1–6 C atoms and can, for example, be substituted by $C_1$–$C_4$-alkoxy, chlorine, cyano, acetoxy, di-($C_1$–$C_2$-alkyl)amino, tri-($C_1$–$C_2$-alkyl)-ammonium, carboxyl, $C_1$–$C_2$-alkoxycarbonyl, carbamoyl, sulpho, acylamino or N-($C_1$–$C_2$-alkyl)acylamino.

Cycloalkyl radicals $R^8$ which may be mentioned are cyclohexyl radicals, which can be substituted by 1–3 methyl groups.

Suitable aryl radicals $R^8$ are, in addition to naphthyl, especially phenyl groups, which, for example, can be substituted by 1–3 methyl, $C_2$–$C_4$-alkyl, cyclohexyl, benzyl, 1–3 chlorine or bromine, 1–2 CF₃, nitro, cyano, carboxyl, $C_1$–$C_2$-alkoxycarbonyl, $C_1$–$C_4$-alkylsulphonyl, sulphamoyl, which is optionally substituted by 1–2 $C_1$–$C_4$-alkyl, or pyrrolidinosulphonyl, piperidinosulphonyl, morpholinosulphonyl, phenoxysulphonyl, acylamino, N—$C_1$—$C_2$—alkyl-acylamino, N-phenylacylamino, 1–2 $C_1$–$C_4$-alkoxy, phenoxy, methylenedioxy, —O—CH₂—O—CH₂—(=fused 1,3-dioxine ring) and/or sulpho.

Examples of heterocyclic radicals $R^8$ are pyridyl, thienyl and sulpholan-3-yl.

Radicals possible as acyl radicals $R^9$ and those in acylamino groups are $C_1$–$C_4$-alkylcarbonyl or $C_1$–$C_2$-alkoxycarbonyl, which are optionally substituted by 1–3 chlorine, aminocarbonyl, which is optionally substituted by $C_1$–$C_4$-alkyl, cyclohexyl, phenyl, toluyl, chlorophenyl or sulphophenyl, di-$C_1$–$C_2$-alkylaminosulphonyl, phenylacetyl, benzoyl- or phenyl-sulphonyl radicals which are optionally substituted by methyl, methoxy or chlorine, $C_1$–$C_4$-alkylsulphonyl which is optionally substituted by chlorine, or formyl or—especially when more than one sulpho group is present in the molecule—also reactive radicals having the character of an acyl group, such as dichlorotriazinyl, difluorotriazinyl, 5-chloro-2,4-difluoro-pyrimidin-6-yl and 2,3-dichloroquinoxalin-6-yl-carbonyl.

Suitable substituents on the divalent radicals L are halogen atoms, such as chlorine and bromine. Thus, 1,2-phenylene radicals can carry, for example, 1–4 chlorine or bromine atoms, or 1,2-ethenylene groups can be substituted by 1–2 chlorine or bromine atoms.

Anions possible as An⊖ are inorganic or organic anions customary in dyestuff chemistry, such as chloride, nitrate, sulphate, bisulphate, phosphate, perchlorate, tetrafluoborate, chlorozincate or acetate, $C_1$-$C_2$-alkylsulphate, $C_1$-$C_4$-alkylphosphonate, toluenesulphonate, lactate or amidosulphonate.

Within the scope of the invention, a particularly preferred group of compounds corresponds to the formula

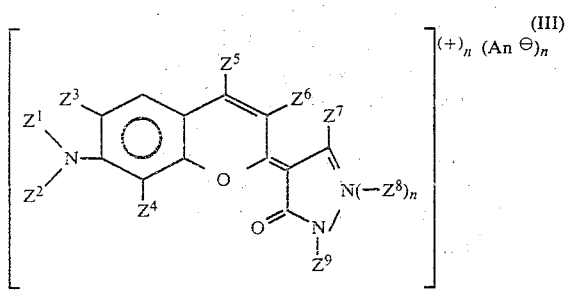

wherein $Z^1$ represents methyl, ethyl, chloroethyl, n-propyl, n-butyl, phenyl-$C_1$-$C_3$-alkyl, sulphophenyl-$C_1$-$C_3$-alkyl, cyclohexyl, phenyl, toluyl, sulphophenyl or sulphotoluyl and $Z^2$ represents hydrogen, methyl, ethyl, chloroethyl, n-propyl, n-butyl, phenyl-$C_1$-$C_3$-alkyl or sulphophenyl-$C_1$-$C_3$-alkyl or $Z^1$ and $Z^2$ together also represent one of the radicals —(CH$_2$)$_4$—, —(CH$_2$)$_5$— or —(CH$_2$)$_2$—O—(CH$_2$)$_2$—, $Z^3$ represents hydrogen or methyl and $Z^4$ represents hydrogen or methyl and $Z^1$ and $Z^3$ together also represent a $C_2$-$C_3$-alkylene radical which is optionally substituted by 1–3 methyl groups and $Z^2$ and $Z^4$ together also represent a n-propylene radical, $Z^5$ represents hydrogen, methyl, o-carboxyphenyl, o-$C_1$-$C_4$-alkoxycarbonylphenyl, phenyl or sulphophenyl, $Z^6$ represents hydrogen, methyl or chlorine, $Z^7$ represents hydrogen, methyl, trifluoromethyl, phenyl or sulphophenyl, $Z^8$ represents methyl, ethyl, n-propyl, n-butyl, β-hydroxyethyl, β-hydroxy-n-propyl, allyl or benzyl, $Z^9$ represents methyl, ethyl, isopropyl, β-acetoxyethyl, β-cyanoethyl, benzyl, phenyl, chlorophenyl, bromophenyl, dichlorophenyl, trichlorophenyl, chlorotoluyl, sulphophenyl, sulphochlorophenyl, nitrophenyl, methylsulphonylphenyl, ethylsulphonylphenyl, p-acetoxyethylsulphonylphenyl, β-sulphatoethylsulphonylphenyl, propylsulphonylphenyl, butylsulphonylphenyl, carboxyphenyl, methoxycarbonylphenyl, ethoxycarbonylphenyl, sulphamoylphenyl, N,N-dimethylsulphamoylphenyl, N,N-diethylsulphamoylphenyl, phenoxysulphonylphenyl or 3-sulpholanyl, n represents the number 0 or 1 and An⊖ represents an anion.

Compounds of particular value industrially are those of the formula

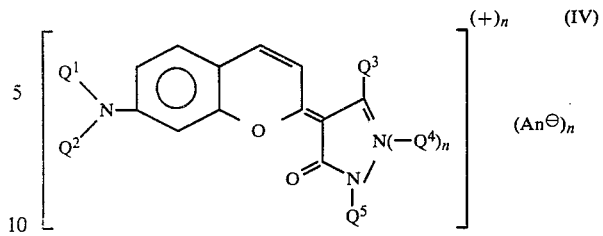

wherein $Q^1$ represents methyl, ethyl, n-propyl, n-butyl, benzyl, sulphobenzyl, β-phenylethyl or sulpho-β-phenylethyl, $Q^2$ has one of the meanings of $Q^1$, $Q^3$ represents methyl, $Q^4$ represents methyl, ethyl, n-propyl, n-butyl, β-hydroxyethyl, β-hydroxy-n-propyl, allyl or benzyl, $Q^5$ represents methyl, ethyl, phenyl, chlorophenyl, dichlorophenyl, trichlorophenyl, bromophenyl, sulphophenyl, sulphochlorophenyl or nitrophenyl, n represents the number 0 or 1 and An⊖ represents an anion.

When n=1,

Q and $Q^2$ preferably represent methyl, ethyl, benzyl or sulphobenzyl, $Q^3$ preferably represents methyl, $Q^4$ preferably represents methyl, ethyl, β-hydroxyethyl or β-hydroxy-n-propyl and $Q^5$ preferably represents methyl, ethyl, phenyl or sulphophenyl.

The dyestuffs of the formula I can be prepared by diverse processes. One of the processes, by which dyestuffs of the nullmethine type described in Research Disclosure 1977, Abstract 16,325 can also advantageously be prepared, is characterised in that compounds of the formula

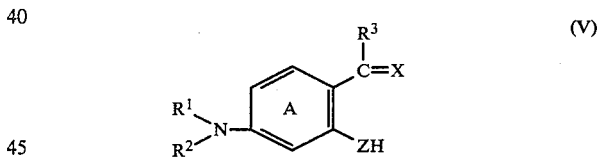

wherein $R^1$, $R^2$, A and Z possess the abovementioned meaning, $R^3$ represents hydrogen, alkyl, aralkyl, aryl, alkoxy, halogen, cyano, carboxyl, alkoxycarbonyl, alkylsulphonyl or arylsulphonyl, X represents =O, =N—$C_6H_5$ or =N⊕(CH$_3$)$_2$An⊖ and An⊖ represents an anion, are subjected to a condensation reaction with compounds of the formula

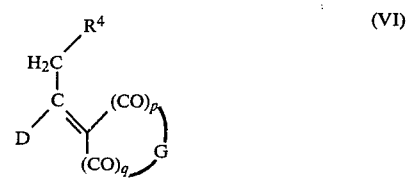

wherein $R^4$, p and q possess the abovementioned meaning,

G represents the remaining members of a carbocyclic or heterocyclic ring system, D represents $-O-W^1$, $-S-W^1$, $-N(W^2W^3)$ or halogen, $W^1$ represents hydrogen or $C_1-C_3$-alkyl and $W^2$ and $W^3$ represent $C_1-C_4$-alkyl or together represent $-(CH_2)_4-$, $-(CH_2)_5-$ or $-(CH_2)_2-O-(CH_2)_2$, with the elimination of water and DH.

Compared with the processes known from Research Disclosure 1977, Abstract 16,325 for the preparation of benzopyranylidene-rhodanine dyestuffs, this process is distinguished by better accessibility, stability and manageability of the starting components and a higher yield of process products.

Halogen radicals D are understood as meaning in particular chlorine, bromine and iodine. Preferably, D represents —OH.

The condensation reaction is appropriately carried out in an inert solvent in the temperature range of 60°–180° C., preferably 80°–150° C.

Inert solvents which can be used are, in addition to inorganic solvents such as sulphuric acid, phosphoric acid or polyphosphoric acid, in particular organic solvents which are able to dissolve the starting components V and VI to a sufficient extent. When non-polar, water-immiscible solvents such as toluene, chlorotoluene, dichlorotoluene, xylene, chlorobenzene or dichlorobenzene are used, it is advisable during the reaction continuously to remove the water formed in the condensation reaction, by azeotropic distillation, for example by boiling under a water separator.

However, polar organic solvents such as glacial acetic acid, isopropanol, n-butanol, ethylene glycol monomethyl ether or ethylene glycol monoethyl ether or dimethylformamide are also suitable.

In the preferred case of D=OH, the condensation reaction is appropriately carried out in the presence of a basic condensing agent and as a rule catalytic amounts suffice. Suitable basic condensing agents are, in addition to alkali metal alcoholates and alkali metal acetates, in particular cyclic secondary amines such as piperidine, pyrrolidine or morpholine. Piperidine is particularly suitable.

Most of the compounds of the formula V are known or are accessible by known methods, especially by reacting a compound of the formula

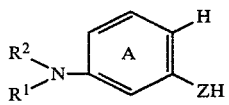
(VII)

wherein $R^1$, $R^2$ and Z have the abovementioned meaning, with known reagents which introduce the $R^3-(C=X)$ group, such as, for example, with the Vilsmeier reagent accessible from dimethylformamide and $POCl_3$ or phosgene, in order to introduce an aldehyde group ($R^3=H$), as is described, for example, in German Offenlegungsschrift (German Published Specification) No. 2,363,459, or with phthalic anhydride, in order to introduce the o-carboxybenzoyl radical.

Suitable compounds of the formula V are, for example, 4-dimethylamino-salicylaldehyde, 4-diethylamino-salicylaldehyde, 4-di-n-butylamino-salicylaldehyde, 4-dibenzylamino-salicylaldehyde, 4-di-β-phenylethylaminosalicylaldehyde, 4-piperidino-salicylaldehyde, 4-di-β-cyanoethylamino-salicylaldehyde, 4-N-benzyl-N-methylamino-salicylaldehyde, di-β-chloroethylamino-salicylaldehyde, N-methyl-N-sulphobenzylamino-salicylaldehyde, di-β-hydroxyethylamino-salicylaldehyde, 7-hydroxy-1,2,2,4-tetramethyl-1,2,3,4-tetrahydroquinoline-6-carbaldehyde, 5-hydroxy-1,8-trimethylene-1,2,3,4-tetrahydroquinoline-6-carbaldehyde, 3-methyl-4-ethylamino-salicylaldehyde, 3,5-dimethyl-4-amino-salicylaldehyde, 4-acetamino-salicylaldehyde-anil, 4-benzenesulphonylamino-salicylaldehyde, 2-amino-4-dimethylamino-benzaldehyde, 4-diethylamino-2-mercaptobenzaldehyde (precursor VII according to J. Org. Chem. 31 (1966) 3,980), 4-diethylamino-2-hydroxy-2'-carboxy-benzophenone, 4-dimethylamino-2-hydroxy-2'-carboxy-benzophenone, 4-diethylamino-2-hydroxy-acetophenone and 4-diethylamino-2-hydroxy-benzophenone, Most of the compounds of the formula VI, especially those in which D=OH, are also known or accessible by known methods, for example by reacting a compound of the formula

(VIII)

which contains an active methylene group and wherein p, q and G possess the abovementioned meaning, with an acylating agent of the formula $R^4-CH_2-COCl$ or $R^4-CH_2-CO-O-CO-CH_2-R^4$ (wherein $R^4$ possesses the above-mentioned meaning).

The C-acylation of pyrazol-5-one compounds with acid chlorides or anhydrides in the presence of calcium hydroxide is described in Acta Chemica Scandinavia 13 (1959) 1,668–70, the C-acylation of barbituric acid derivatives is described in Chemische Berichte 54 (1921) 1,048 et seq. and the C-acylation of 4-hydroxycoumarin with carboxylic acids and $POCl_3$ is described in Archiv der Pharmazie 268 (1955) 356–361. 2-Acetyl-indane-1,3-dione is prepared according to Ind. Eng. Chem. 34 (1942) 494-7 by a condensation reaction of dimethyl phthalate with acetone in the presence of sodium ethylate. In J. Chem. Soc. (London) 1948, 51, sodium amide is recommended as the condensing agent for the same reaction. 2-Acetyl-perinaphthindane-1,3-dione and 2-acetyl-periacenaphthindane-1,3-dione can also be obtained by the same method. In place of acetone it is also possible, according to Ind. Eng. Chem. 34 (1942) 494, to subject other methyl alkyl ketones to a condensation reaction to give 2-acyl-indane-1,3-diones, with equal success.

The C-acyl compounds of the formula VI in which D=OH can exist in several different tautomeric structures:

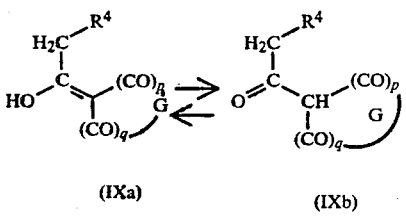

(IXa)          (IXb)

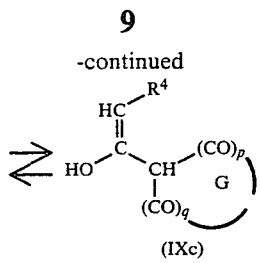

For 1-phenyl-3-methyl-4-acetyl-pyrazol-5-ones, the colourless keto form IX b, which is obtainable from polar solvents, in addition to the yellowish enol form a or o, which can be isolated from non-polar solvents, are described in Acta Chemica Scandinavia 13 (1959) 1,668–70. All the tautomeric forms are equally suitable for the condensation reaction, according to the invention, with V.

Functional derivatives of IXa–c, such as are covered by formula VI (D=OH), such as enol ethers, enthiols, enol-thioethers, enamines and enhalides, are accessible from IX a–c by known processes. Preferred functional derivatives are enamines, in which D represents N-morpholino, N-piperidino or N-pyrrolidino. These are easily obtained from IX a–c and morpholine, piperidine and pyrrolidine in water-immiscible solvents such as toluene, xylene, chlorobenzene or chloroform, by boiling under a water separator.

Suitable compounds of the formula VI are, for example: 1-phenyl-3-methyl-4-acetyl-pyrazol-5-one, 1,3-dimethyl-4-acetyl-pyrazol-5-one, 1-methyl-3-phenyl-4-acetyl-pyrazol-5-one, 1-p-chlorophenyl-3-methyl-4-propionyl-pyrazol-5-one, 1-p-toluyl-3-methyl-4-chloroacetylpyrazol-5-one, 1-m-chlorophenyl-3-methyl-4-nitroacetylpyrazol-5-one, 1-(2′,5′-dichlorophenyl)-3-p-methoxyphenyl-4-acetyl-pyrazol-5-one, 1-(2′,4′,6′-trichlorophenyl)-3-N-acetyl-N-anilino-4-acetyl-pyrazol-5-one, 1-p-carboxyphenyl-3-methyl-4-acetyl-pyrazol-5-one, 1-p-methoxycarbonylphenyl-3-methyl-4-acetyl-pyrazol-5-one, 1-p-ethoxycarbonylphenyl-3-methyl-4-acetyl-pyrazol-5-one, 1-p-methylsulphonyl-phenyl-3-methyl-4-acetyl-pyrazol-5-one, 1-p-n-butylsulphonylphenyl-3-methyl-4-acetyl-pyrazol-5-one, 1-p-nitrophenyl-3-methyl-4-acetyl-pyrazol-5-one, 1-p-sulphamoylphenyl-3-methyl-4-acetyl-pyrazol-5-one, 1-(2′,6′-dichloro-4′-dimethylaminosulphonylphenyl)-3-methyl-4-acetyl-pyrazol-5-one, 1-p-cyanophenyl-3-methyl-4-acetyl-pyrazol-5-one, 1-p-carbamoylphenyl-3-N-acetyl-N-p-toluidino-4-acetyl-pyrazol-5-one, 1-p-piperidinosulphonylphenyl-3-methyl-4-acetyl-pyrazol-5-one, 1-p-morpholinosulphonylphenyl-3-methyl-4-acetyl-pyrazol-5-one, 1-phenyl-3-carboxy-4-acetyl-pyrazol-5-one, 1-isopropyl-3-methoxycarbonyl-4-acetyl-pyrazol-5-one, 1-benzyl-3-ethoxycarbonyl-4-acetyl-pyrazol-5-one, 1-phenyl-3-cyano-4-acetyl-pyrazol-5-one, 1-phenyl-3-carbamoyl-4-acetylpyrazol-5-one, 1-p-chlorophenyl-3-methoxy-4-acetyl-pyrazol-5-one, 1-p-bromophenyl-3-chloro-4-acetyl-pyrazol-5-one, 1-β-acetoxyethyl-3-p-chlorophenyl-4-acetyl-pyrazol-5-one, 1-(2′,4′-dichloro-6′-methoxyphenyl)-3-methyl-4-acetyl-pyrazol-5-one, 1-phenyl-3-trifluoromethyl-4-acetyl-pyrazol-5-one, 1-phenyl-3-N-acetyl-N-p-anisidino-4-acetylpyrazol-5-one, 1-phenyl-3-N-acetyl-N-p-chloroanilino-4-acetyl-pyrazol-5-one, 1-phenyl-3-N-acetyl-N-p-trifluoromethylanilino-4-acetyl-pyrazol-5-one, 1-phenyl-3-N-acetyl-N(3′,4′-dichloro-anilino)-4-acetyl-pyrazol-5-one, 1-phenyl-3-N-acetyl-N-(3′,4′-methylenedioxyanilino)-4-acetylpyrazol-5-one, 1-phenyl-3-N-acetyl-N(1′,3′-benzodioxin-6-ylamino)-4-acet-yl-pyrazol-5-one, 1-(3′-sulpholanyl)-3-N-acetyl-N-(3′-chloro-4′-methyl-anilino)-4-acetyl-pyrazol-5-one, 1-phenyl-3-N-acetyl-N-p-acetanilino-4-acetyl-pyrazol-5-one, 1-methyl-3-N-acetyl-N-p-phenetidino-4-acetyl-pyrazol-5-one, 1-phenyl-3-N-acetyl-N-p-nitroanilino-4-acetylpyrazol-5-one, 1-phenyl-3-N-acetyl-N-p-methylsulphonyl-4-acetyl-pyrazol-5-one, 1-phenyl-3-acetylamino-4-acetylpyrazol-5-one, 1-phenyl-3-N-ethoxycarbonyl-N-anilino-4-acetyl-pyrazol-5-one, 1-phenyl-3-p-toluyl-4-acetyl-pyrazol-5-one, 1-phenyl-3-(2′,4′-xylyl)-4-acetyl-pyrazol-5-one, 1-(3′-sulpholanyl)-3-methyl-4-acetyl-pyrazol-5-one, 1-p-[6′-methylbenzthiazol-2′-yl]-phenyl-3-methyl-4-acetyl-pyrazol-5-one, 1,2,3-trimethyl-4-acetyl-5-oxo-pyrazolium methosulphate and 1-phenyl-2,3-dimethyl-4-acetyl-5-oxopyrazolium methosulphate and also: 1,3-dimethyl-5-acetyl-barbituric acid, 1,3-dibutyl-5-acetyl-barbituric acid, 1,3-dibenzyl-5-acetyl-barbituric acid, 1,3-diphenyl-5-acetyl-barbituric acid, 1,3-diallyl-5-acetyl-barbituric acid, 1,3-dibutyl-5-acetyl-thiobarbituric acid, 1-butyl-3-methyl-5-acetylbarbituric acid, 1-phenyl-3-butyl-5-acetyl-barbituric acid, 1-phenyl-5-acetyl-barbituric acid, 1-cyclohexyl-5-acetylbarbituric acid, 1-benzyl-5-propionyl-barbituric acid, 1-benzyl-5-chloroacetyl-barbituric acid, 5-acetylbarbituric acid, 1-methyl-2,6-dioxo-3-methylaminocarbonyl-4-hydroxy-5-acetyl-2H.6H-pyridine, 1-ethyl-2,6-dioxo-3-cyano-4-hydroxy-5-acetyl-2H.6H-pyridine, 1-β-methoxyethyl-2,6-dioxo-3-ethoxycarbonyl-4-hydroxy-5-acetyl-2H.6H-pyridine, 1-methyl-2-phenyl-4,6-dioxo-5-acetyl-4H.6H-pyrimidine, dehydroacetic acid, 3-acetyl-4-hydroxy-coumarin, 3-phenylacetyl-4-hydroxy-coumarin, 1-methyl-3-acetyl-4-hydroxyquinol-2-one, 1,3-diphenyl-4,6-dioxo-5-acetyl-tetrahydropyridazine, 2-acetylindane-1,3-dione, 2-acetyl-4-nitroindane-1,3-dione, 2-acetyl-4,5,6,7-tetrachloro-indane-1,3-dione, 2-propionyl-4-acetamino-indane-1,3-dione, 2-acetylperinaphthindane-1,3-dione, 2-acetyl-periacenaphthindane-1,3-dione, 2-acetyl-3-hydroxy-benzo[b]furane, 2-acetyl-2-hydroxy-benzo[b]furane, 2-acetyl-3-hydroxy-benzo[b]thiophene, 3-acetyl-2-hydroxy-benzo[b]thiophene, 1-ethyl-2-acetyl-3-hydroxy-indole, 3-phenyl-4-acetyl-isoxazol-5-one, 2-phenyl-4-acetyl-oxazol-5-one, 3-ethyl-4-oxo-5-acetyl-thiazoline-2-thione, 2-phenyl-5-acetyl-thiazolin-4-one, 2-benzylmercapto-4-acetyl-thiazolin-5-one, 2-p-toluyl-4,6-dioxo-5-acetyl-4H.6H-1,3-thiazine, 2,4-dioxo-3-acetyl-2H.4H-pyrido[1.2-a]pyrimidine, 1-methyl-2,4-dioxo-3-acetyl-2H.4H-pyrido[1.2-a]pyrimidinium methosulphate, 6-acetyl-5,7-dioxo-5H.7H-thiazolo[3.2-a]pyrimidine, 3-acetyl-2,4-dioxo-2H.4H-pyrimido[1.2-a]pyrimidine, 2-acetyl-5,5-dimethyldihydroresorcinol and 5-cyano-6-hydroxy-7-acetyl-8-oxo-2,3-benzo-8H-imidazo[1.2-a]pyridine.

A second process for the preparation of compounds of the formula I is characterized in that compounds of the formula

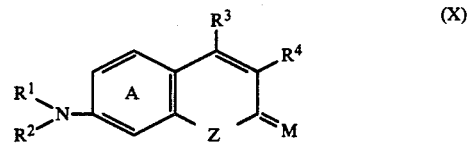

wherein

R$^1$–R$^4$, A and Z have the abovementioned meaning,
M represents =S or =N—W and W represents hydrogen, $C_1$-$C_4$-alkyl, benzyl, cyclohexyl, phenyl, toluyl, chlorophenyl, methoxyphenyl, $C_1$-$C_3$-alkylcarbonyl, $C_1$-$C_2$-alkoxycarbonyl or benzoyl, are subjected to a condensation reaction with compounds of the formula

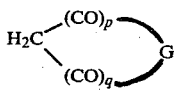   (VIII)

wherein p, q and G possess the abovementioned meaning, and elimination of $H_2M$.

The condensation reaction is appropriately carried out in an inert organic solvent in the temperature range of 80°–200° C., preferably 100°–160° C. Suitable inert organic solvents are higher-boiling solvents which have a boiling point above 90° C., such as ethylene glycol monomethyl ether, ethylene glycol monoethyl ether, ethylene glycol diacetate, ethylene glycol, ethylene glycol dimethyl ether, ethylene glycol diethyl ether, dimethylformamide, dimethylacetamide, acetic anhydride, chlorobenzene, o-dichlorobenzene, xylene and chlorotoluenes.

Most of the compounds of the formula X are known or are accessible by known methods, for example according to German Offenlegungsschriften (German Published Specifications) Nos. 1,619,567, 2,010,492, and 2,129,565 and Japanese Patent No. 2,042,880.

Suitable examples of compounds of the formula X are: 2-imino-3-cyano-7-diethylamino-2H-benzo[b]pyrane, 2-phenylimino-3-carboxy-7-dimethylamino-2H-benzo[b]pyrane, 2-benzylimino-3-methoxycarbonyl-7-di-n-butylamino-2H-benzo[b]pyrane, 2-p-toluylimino-3-phenyl-7-N-benzyl-N-methyl-2H-benzo[b]pyrane, 2-p-chlorophenylimino-3-methylcarbamoyl-7-diethylamino-2H-benzo[b]pyrane, 2-p-methoxyphenylimino-3-methylsulphonyl-7-dimethylamino-2H-benzo[b]pyrane, 2-ethylamino-3-nitro-7-di-n-propylamino-2H-benzo[b]pyrane, 2-cyclohexylimino-3-p-toluyl-7-dibenzylamino-2H-benzo[b]pyrane, 2-n-butylimino-3-nitro-7-diethylamino-2H-benzo[b]pyrane, 3-p-chlorophenyl-7-piperidino-2H-benzo[b]pyrane-2-thione, 2-imino-3-p-nitrophenyl-7-diethylamino-2H-benzo[b]pyrane, 1-methyl-7-dimethylamino-1H.2H-quinoline-2-thione, 2-imino-3-cyano-7-acetamino-2H-benzo[b]pyrane, 2-phenylimino-3-cyano-7-diethylamino-2H-benzo[b]thiopyrane, 2-imino-3-[4'-chloropyrazol-1'-yl]-7-dimethylamino-2H-benzo[b]pyrane, 2-methylimino-3-[1',2',4'-triazol-1'-yl]-7-diethylamino-2H-benzo[b]pyrane and 2-ethoxycarbonylimino-3-phenyl-7-diethylamino-2H-benzo[b]pyrane.

Suitable examples of compounds of the formula VII are those which have been listed for IXa-c (or VI), but in each case without the acyl group $R^4$—$CH_2CO$—.

A varient of the second process for the preparation of compounds of the formula I is characterized in that compounds of the formula

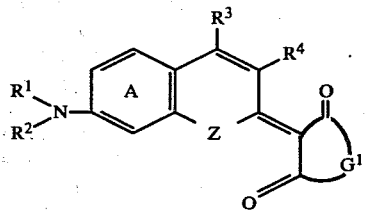   (XI)

wherein
$R^1$–$R^4$, A, Z and $An^-$ possess the abovementioned meaning and
E represent —S—$C_1$—$C_2$—alkyl or —O—$C_1$—$C_2$—alkyl, are subjected to a condensation reaction with compounds of the formula VIII and elimination of EH and in some cases HAn.

The condensation reaction is appropriately carried out in an inert organic solvent in the temperature range of 80°–200° C., preferably 100°–160° C., preferably in the presence of an acid-binding agent such as triethylamine, pyridine, tributylamine, morpholine, diethylamine, quinoline or sodium acetate, potassium carbonate, sodium bicarbonate or magnesium oxide. Suitable solvents amongst the abovementioned liquids are in particular the polar, water-miscible solvents and also acetic anhydride.

A further process is suitable for the preparation of particular representatives of compounds of the formula I in which p and q are both 1 and G=$G^1$ and represents a radical of the indane-1,3-dione, perinaphthindane-1,3-dione or periacenaphthindane-1,3-dione series (formula XII).

A process for the preparation of compounds of the formula

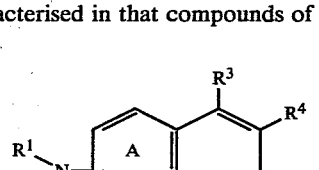   (XII)

wherein
$R^1$–$R^4$, A and Z have the abovementioned meaning and
$G^1$ represents a radical of the indane-1,3-dione, perinaphthindane-1,3-dione or acenaphthindane-1,3-dione series,
is characterised in that compounds of the formula

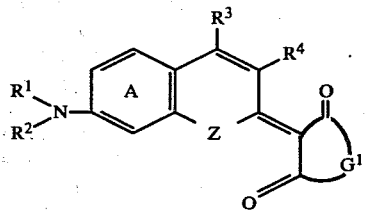   (XIII)

wherein $R^1$–$R^4$, A and Z possess the abovementioned meaning, or a tautomer of this compound or an acid salt thereof, are subjected to a condensation reaction with anhydrides of the formula

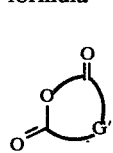   (XIV)

wherein $G^1$ possesses the abovementioned meaning.

The condensation reaction is carried out in the temperature range of 140°–240° C., preferably 160°–220° C., either in the melt or in a high-boiling organic solvent. The water formed during the condensation reaction is appropriately distilled off continuously, optionally together with a little solvent. Suitable solvents are high-boiling liquids such as dichlorotoluenes, trichlorobenzenes, o-dichlorobenzene, nitrobenzene, a mixture of diphenyl and diphenyl ether, N-methylpyrrolidone, diethylene glycol diethyl ether or quinoline.

Suitable compounds of the formula XIII are, for example, 7-diethylamino-2-methylene-benzo[b]pyrane or the HCl salt of this compound, 7-dimethylamino-4-methyl-2-methylene-benzo[b]pyrane or the HClO₄ salt of this compound, 7-dimethylamino-2-methylquinoline, 7-diethylamino-2,4-dimethylquinoline, 7-diethylamino-2,6-dimethylquinoline and 7-dimethylamino-1-methyl-2-methylene-quinoline.

The acid salts of compounds of the formula XIII are obtained, for example, by a condensation reaction of compounds of the formula VII with 1,3-dicarbonyl compounds of the formula R³—CO—CH(R⁴)—CO—CH₃ (XV) or with derivatives of these compounds, such as acetals, anils or enamines, in an acid medium, for example in boiling glacial acetic acid.

Suitable examples of compounds of the formula VII are the substances listed for V, but in each case without the acyl group R³—CO—. Suitable 1,3-dicarbonyl compounds are, for example, 1,1,3,3-tetramethoxypropane, 1,1-diethoxy-butan-3-one and acetylacetone.

The free methylene bases of the formula XIII can be liberated from the acid salts in a conventional manner with the aid of acid-binding agents such as sodium hydroxide solution.

Nitro, sulpho and chlorosulphonyl groups and halogen atoms can advantageously also be introduced subsequently with the aid of known electrophilic reagents, such as nitrating acid, oleum or chlorosulphonic acid, or with halogenating agents such as SO₂Cl₂ or bromine, the electrophilic substitution preferably taking place in suitable aryl or anilino substituents which may be present, such as phenyl, toluyl, xylyl, methoxyphenyl, ethoxyphenyl, acetaminophenyl or chlorophenyl, in the corresponding anilino derivatives and/or in a free position R⁴.

The dyestuffs of the formula I are suitable for dyeing and printing natural, semi-synthetic and synthetic fibre and fabric materials and can also be used as laser dyestuffs.

Whilst the dyestuffs containing sulpho groups are particularly suitable for dyeing and printing polyamide, polyurethane and wool fibres and the cationic compounds free from acid groups are preferentially suitable for fibres containing acid groups, such as polyacrylonitrile, acid-modified polyesters and acid-modified polyamides, the dyestuffs of the formula I which are free from ionic groups conferring solubility in water are disperse dyestuffs for dyeing and printing polyester, polyamide, polyurethane, cellulose 2½-acetate, cellulose triacetate, polypropylene and polyacrylonitrile fibres.

Clear dyeings, which in some cases are very brilliant, in yellow to violet shades are produced by the dyestuffs, according to the invention, of the formula I on the said fibres and fabrics and these dyeings are distinguished by good fastness properties in use.

Amongst the preferred dyestuffs of the formula II, the cationic representatives in which n=1 as a rule display an orange-red fluorescence and are suitable as fluorescent dyestuffs and as laser dyestuffs. Similar fluorescent characteristics are displayed by the neutral and acid dyestuffs of the formula II in which R⁵ represent a N-acyl radical. These dyestuffs also can advantageously be used as fluorescent dyestuffs and as laser dyestuffs.

Neutral compounds of the formula I which are free from radicals which increase the fastness to sublimation, such as sulphamoyl and carbamoyl groups, can also advantageously be employed in the transfer printing process.

EXAMPLE 1

174 g of 1-phenyl-3-methyl-pyrazol-5-one in 700 ml of acetic anhydride, with the addition of 6 g of p-toluenesulphonic acid, are heated to the boil under reflux for 6 hours. The solvent is then distilled off under a water-pump vacuum, the residue is dissolved hot in 2 l of 5% strength sodium hydroxide solution, the solution is clarified with 8 g of active charcoal, the filtrate is acidified with hydrochloric acid at room temperature and the crystalline precipitate is filtered off, washed with water and dried in vacuo at 40° C. 183 g of 1-phenyl-3-methyl-4-acetyl-pyrazol-5-one are obtained in the form of colourless crystal needles.

32.4 g of this compound and 30 g of 4-diethylaminosalicylaldehyde in 75 ml of xylene, with the addition of 1.5 ml of piperidine, are heated to the boil under a water separator for 3 hours. After cooling, the crystalline precipitate is filtered off, washed with ethanol and dried in vacuo at 70° C. 34 g of the compound of the formula

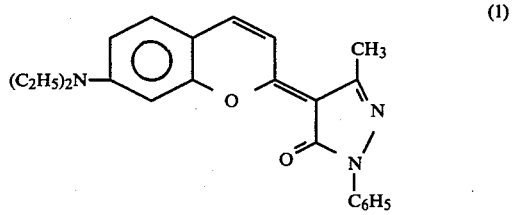

(1)

are obtained in the form of dark red crystal needles. The dyestuff dyes polyester by the high temperature process (130° C.) in a clear yellowish-tinged red shade with good fastness properties.

The dyestuffs indicated in the table which follows are prepared in an analogous manner from the corresponding starting compounds. They possess similar coloristic properties.

Compound of the formula

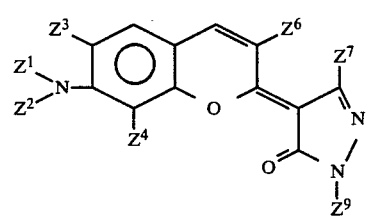

Dyeing process:
HT=130° C. (autoclave)
Th=Thermosolve process (fixing temperature: 220° C.)

| No. | $Z^1$ | $Z^2$ | $Z^3$ | $Z^4$ | $Z^6$ | $Z^7$ | $Z^9$ | Colour shade (polyester) | |
|---|---|---|---|---|---|---|---|---|---|
| (2) | $C_2H_5$ | $C_2H_5$ | H | H | H | $C_6H_5$ | $C_6H_5$ | red | HT |
| (3) | $C_2H_5$ | $C_2H_5$ | H | H | H | $CH_3$ | $CH_3$ | Yellowish-tinged red | " |
| (4) | $C_2H_5$ | $C_2H_5$ | H | H | H | $C_6H_5$ | $CH_3$ | yellowish-tinged red | " |
| (5) | $C_2H_5$ | $C_2H_5$ | H | H | H | $CH_3$ | $C_6H_4Cl$-(2) | bluish-tinged scarlet | " |
| (6) | $C_2H_5$ | $C_2H_5$ | H | H | H | $CH_3$ | $C_6H_3Cl_2$-(2,5) | bluish-tinged scarlet | " |
| (7) | $C_2H_5$ | $C_2H_5$ | H | H | H | $CH_3$ | $C_6H_4CH_3$-(4) | yellowish-tinged red | " |
| (8) | $C_2H_5$ | $C_2H_5$ | H | H | H | $C_6H_4OCH_3(4)$ | $C_6H_5$ | red | " |
| (9) | $CH_3$ | $CH_3$ | H | H | H | $CH_3$ | $CH_3$ | yellowish-tinged red | " |
| (10) | n-$C_3H_7$ | n-$C_3H_7$ | H | H | H | $CH_3$ | $C_6H_4Cl$-(2) | bluish-tinged scarlet | " |
| (11) | n-$C_4H_7$ | n-$C_4H_7$ | H | H | H | $CH_3$ | $C_6H_3Cl_2$-(2,5) | bluish-tinged scarlet | " |
| (12) | $C_6H_5$—$CH_2$ | $C_6H_5CH_2$ | H | H | H | $CH_3$ | $C_6H_4Cl$-(4) | yellowish-tinged red | " |
| (13) | $C_6H_5CH_2$—$CH_2$ | $C_6H_5CH_2$—$CH_2$ | H | H | H | $CH_3$ | $C_6H_5$ | yellowish-tinged red | " |
| (14) | $C_6H_5CH_2$ | $C_2H_5$ | H | H | H | $CH_3$ | $C_6H_4$—Br(4) | yellowish-tinged red | " |
| (15) | $C_2H_5$ | $C_2H_5$ | H | H | $CH_3$ | $CH_3$ | $C_6H_5$ | orange | " |
| (16) | $C_2H_5$ | $C_2H_5$ | H | Cl | H | $CH_3$ | $C_6H_5$ | orange | " |
| (17) | $C_2H_5$ | $C_2H_5$ | H | H | H | $CF_3$ | $C_6H_5$ | yellowish-tinged red | " |
| (18) | Cl—$CH_2$—$CH_2$ | Cl—$CH_2$—$CH_2$ | H | H | H | $CH_3$ | $CH(CH_3)_2$ | yellowish-tinged red | " |
| (19) | —$(CH_2)_5$— | | H | H | H | H | $C_6H_5$ | yellowish-tinged red | " |
| (20) | —$(CH_2)_2O(CH_2)_2$— | | H | H | H | H | $C_6H_4CH_3$-(2) | yellowish-tinged red | " |
| (21) | —$(CH_2)_4$— | | H | H | H | $CH_3$ | $C_6H_4Cl$-(4) | yellowish-tinged red | " |
| (22) | $C_2H_5$ | H | $CH_3$ | H | H | $CH_3$ | $C_2H_5$ | red-orange | " |
| (23) | n-$C_4H_9$ | n-$C_4H_9$ | H | H | H | $CH_3$ | $C_6H_3CH_3$-(3)-Cl(4) | yellowish-tinged red | Th |
| (24) | $C_2H_5$ | $C_2H_5$ | H | H | H | $CH_3$ | $C_6H_4NO_2$-(4) | bluish-tinged scarlet | " |
| (25) |  | $C_2H_5$ | H | H | H | $CH_3$ | $C_6H_4SO_2CH_3$-(4) | clear orange | " |
| (26) | $C_6H_5(CH_2)_3$ | $C_6H_5(CH_2)_3$ | H | H | H | $CH_3$ | $C_6H_4SO_2(CH_2)_3CH_3$-(4) | clear orange | " |
| (27) | $C_2H_5$ | H | H | $CH_3$ | H | $CH_3$ | $C_6H_4COOCH_3$-(4) | clear orange | " |
| (28) | $C_2H_5$ | $C_2H_5$ | H | H | H | $CH_3$ | $C_6H_4COOC_2H_5(4)$ | clear orange | " |
| (29) | $C_2H_5$ | $C_2H_5$ | H | H | H | $CH_3$ | $C_6H_2Cl_3$-(2.4.6) | brilliant scarlet | " |
| (30) | $C_2H_5$ | $C_2H_5$ | H | H | H | $CH_3$ | $C_6H_4SO_2N(C_2H_5)_2$-(4) | clear orange | " |
| (31) | $C_2H_5$ | $C_2H_5$ | H | H | H | $CH_3$ | $C_6H_4SO_2N(CH_3)_2$-(4) | clear orange | " |
| (32) | $C_2H_5$ | $C_2H_5$ | H | H | H | $CH_3$ | $C_6H_4COOH$-(4) | orange | " |
| (33) | $C_2H_5$ | $C_2H_5$ | H | H | H | $CH_3$ | $C_6H_4SO_2NH_2$-(4) | clear orange | " |
| (34) | $C_2H_5$ | $C_2H_5$ | H | H | H | $CH_3$ | $C_6H_5SO_2OC_6H_5$-(4) | clear orange | " |
| (35) | $C_2H_5$ | $C_2H_5$ | H | H | H | $CH_3$ | $C_2H_4OCOCH_3(4)$ | yellowish-tinged red | HT |
| (36) | $C_2H_5$ | $C_2H_5$ | H | H | H | $CH_3$ | $C_6H_5CH_2$ | yellowish-tinged red | " |
| (37) | $C_2H_5$ | $C_2H_5$ | H | H | H | $CH_3$ | 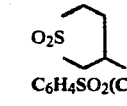 | yellowish-tinged red | " |
| (38) | $C_2H_5$ | $C_2H_5$ | H | H | H | $CH_3$ | $C_6H_4SO_2(CH_2)OCOCH_3$-(4) | clear orange | Th |
| (39) |  | $CH_3$ | H | H | H | $CH_3$ | $C_6H_5$ | red | HT |

-continued

| No. | $Z^1$ | $Z^2$ | $Z^3$ | $Z^4$ | $Z^6$ | $Z^7$ | $Z^9$ | Colour shade (polyester) | |
|---|---|---|---|---|---|---|---|---|---|
| (40) | CH₃—⟨O⟩ | $C_2H_5$ | H | H | H | $CH_3$ | $C_6H_4Cl$-(2) | yellowish-tinged red | " |
| (41) | $C_2H_5$ | $C_2H_5$ | H | H | H | $-\underset{\underset{C_6H_5}{\mid}}{N}-COCH_3$ | $C_6H_4Cl$-(4) | clear strongly bluish-tinged red | Th | and also the compounds

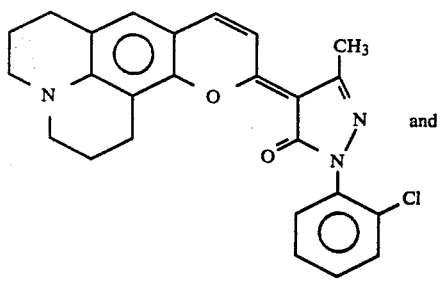

(42)
clear bluish-tinged scarlet
(polyester, HT)

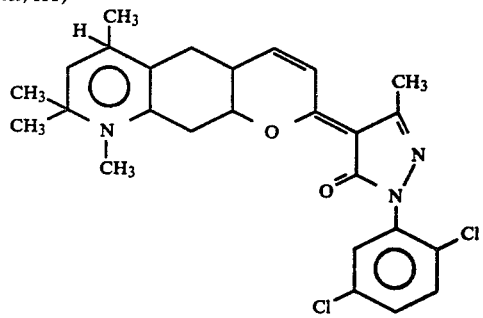

(43)
clear bluish-tinged scarlet
(polyester, HT)

EXAMPLE 44

18 g of the compound of the formula (3) are dissolved in 250 ml of chlorobenzene, with warming, 10 ml of dimethyl sulphate are added at 60°–70° C. and the mixture is warmed at 70° C. for 10 hours and then cooled. The crystalline precipitate is filtered off, washed with toluene and recrystallised from 800 ml of isopropanol. 15 g of the quaternary salt of the formula

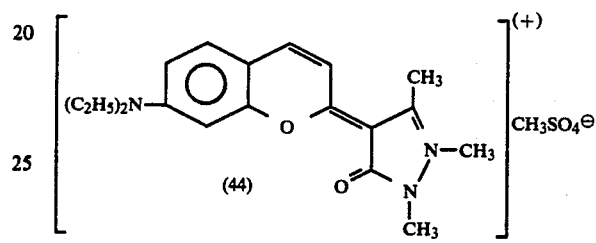

are obtained in the form of blue-violet crystals. A dilute chloroform solution displays strong orange-red fluorescence. An intensive, fluorescent bluish-tinged red dyeing with good fastness properties is obtained on polyacrylonitrile. The dyestuff is suitable as a laser dyestuff.

The following quaternary salts, which also fluoresce strongly, are prepared in an analogous manner:

Compounds of the formula

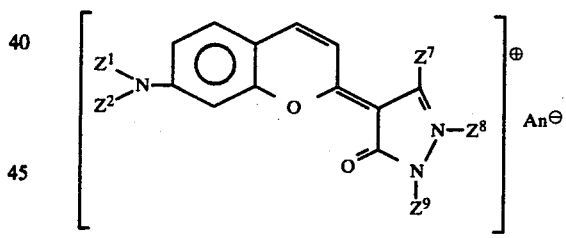

| No. | $Z^1$ | $Z^2$ | $Z^7$ | $Z^8$ | $Z^9$ | $An^\ominus$ | Reaction conditions | Colour shade (PAN) |
|---|---|---|---|---|---|---|---|---|
| (45) | $C_2H_5$ | $C_2H_5$ | $CH_3$ | $CH_3$ | $C_6H_5$ | $CH_3SO_4^\ominus$ | 120 hrs at 80° C. | fluorescent bluish-tinged red |
| (46) | $C_2H_5$ | $C_2H_5$ | $CH_3$ | $C_2H_5$ | $CH_3$ | $C_2H_5SO_4^\ominus$ | 15 hrs at 80° C. | fluorescent bluish-tinged red |
| (47) | $C_2H_5$ | $C_2H_5$ | $CH_3$ | $n-C_3H_7$ | $CH_3$ | $Br^\ominus$ | 10 hrs at 120° C. (autoclave) | fluorescent bluish-tinged red |
| (48) | $C_2H_5$ | $C_2H_5$ | $CH_3$ | $n-C_4H_9$ | $CH_3$ | $Br^\ominus$ | 10 hrs at 135° C. | fluorescent bluish-tinged red |
| (49) | $C_2H_5$ | $C_2H_5$ | $CH_3$ | $C_6H_5CH_2$ | $CH_3$ | $Br^\ominus$ | 5 hrs at 140° C. | fluorescent bluish-tinged red |
| (50) | $C_2H_5$ | $C_2H_5$ | $CH_3$ | $CH_2=CH-CH_2$ | $CH_3$ | $Br^\ominus$ | 7 hrs at 135° C. (autoclave) | fluorescent bluish-tinged red |
| (51) | $C_2H_5$ | $C_2H_5$ | $CH_3$ | $(CH_2)_2OH$ | $CH_3$ | $OCOCH_3^\ominus$ | ethylene oxide glacial acetic acid 3 hrs at 90° C. | fluorescent bluish-tinged red |
| (52) | $C_2H_5$ | $C_2H_5$ | $CH_3$ | $CH_2-CH-CH_3$ $\quad\quad\;\;\, OH$ | $CH_3$ | $OCOCH_3^\ominus$ | propylene oxide glacial acetic acid 3 hrs at 90° C. | fluorescent bluish-tinged red |
| (53) | $n-C_4H_9$ | $n-C_4H_9$ | $CH_3$ | $CH_3$ | $CH_3$ | $CH_3SO_4^\ominus$ | 8 hrs at 80° C. | fluorescent bluish-tinged red |
| (54) | $n-C_3H_7$ | $n-C_3H_7$ | $CH_3$ | $C_2H_5$ | $CH_3$ | $C_2H_5SO_4^\ominus$ | 15 hrs at 85° C. | fluorescent bluish-tinged red |
| (55) | $CH_3$ | $CH_3$ | $CH_3$ | $CH_3$ | $C_2H_5$ | $CH_3SO_4^\ominus$ | 8 hrs at 80° C. | fluorescent bluish-tinged red |
| (56) | $C_6H_5CH_2$ | $C_6H_5CH_2$ | $CH_3$ | $C_2H_4COOCH_3$ | $CH_3$ | $CH_3SO_4^\ominus$ | 8 hrs at 80° C. | fluorescent bluish-tinged red |
| (58) | $C_2H_5$ | $C_2H_5$ | $CH_3$ | $CH_3$ | $CH_3$ | $Cl^\ominus$ | $CH_2=CH-COOCH_3$ glacial acetic acid, HCl 10 hrs at 95° C. | fluorescent bluish-tinged red |
| (59) | | 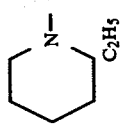 | $CF_3$ | $CH_3$ | $CH_3$ | $p-Tos^\ominus$ | 20 hrs at 135° C. | fluorescent bluish-tinged red |
| (60) | $C_2H_5$ | $C_2H_5$ | H | $CH_3$ | $CH_3$ | $CH_3SO_4^\ominus$ | 10 hrs at 75° C. | fluorescent bluish-tinged red |
| (61) | $C_2H_5$ | $C_2H_5$ | $CH_3$ | $CH_3$ | $CH(CH_3)_2$ | $CH_3SO_4^\ominus$ | 10 hrs at 70° C. | fluorescent bluish-tinged red |

-continued

| No. | $Z^1$ | $Z^2$ | $Z^7$ | $Z^8$ | $Z^9$ | $An^\ominus$ | Reaction conditions | Colour shade (PAN) |
|---|---|---|---|---|---|---|---|---|
| (62) | $C_2H_5$ | $C_2H_5$ | $CH_3$ | $CH_3$ | $CH_2-CH_2-CN$ | $CH_3SO_4^\ominus$ | 10 hrs at 75° C. | fluorescent bluish-tinged red |
| (63) | $C_2H_5$ | $C_2H_5$ | $CH_3$ | $CH_2=CH-CH_2-$ | $CH_2-CH_2OH$ | $Br^\ominus$ | 7 hrs at 135° C. (autoclave) | fluorescent bluish-tinged red |
| (64) | $C_2H_5$ | $C_2H_5$ | $CH_3$ | $CH_3$ | $C_6H_5CH_2$ | $CH_3SO_4^\ominus$ | 10 hrs at 75° C. | fluorescent bluish-tinged red |
| (65) | $C_2H_5$ | $C_2H_5$ | $CH_3$ | $CH_3$ | $CH_2-CH_2-OCCH_3$ (O) $CH_3$ | $CH_3SO_4^\ominus$ | 10 hrs at 75° C. | fluorescent bluish-tinged red |
| (66) | $Cl-CH_2-CH_2$ | $C_2H_5$ | $C_6H_4Cl(4)$ | $CH_3$ | $CH_3$ | $CH_3SO_4^\ominus$ | 10 hrs at 75° C. | fluorescent bluish-tinged red |
| (67) | $C_2H_5$ | $C_2H_5$ | $C_6H_5$ | $CH_3$ | $C_6H_5$ | $CH_2SO_4^\ominus$ | 120 hrs at 80° C. | fluorescent bluish-tinged red |
| (68) | $C_2H_5$ | $C_2H_5$ | $CH_2Cl$ | $CH_3$ | $CH_3$ | $CH_3SO_4^\ominus$ | 10 hrs at 80° C. | fluorescent bluish-tinged red |
| (69) | $C_2H_5$ | $C_2H_5$ | $CH_3$ | $CH_3$ | (tetrahydrothiophene $O_2S$) | $CH_3SO_4^\ominus$ | 15 hrs at 80° C. | fluorescent bluish-tinged red |

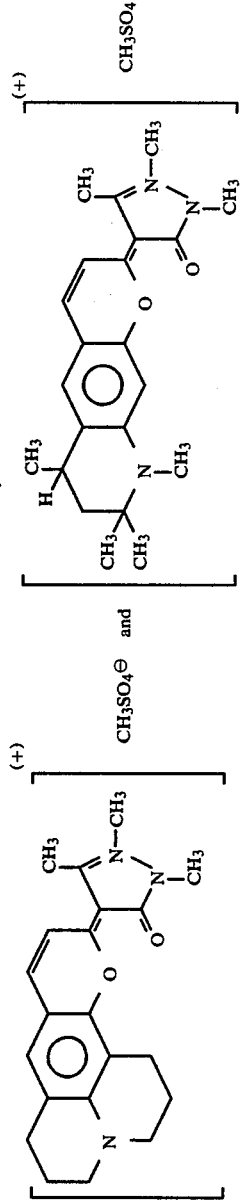

EXAMPLE 72

10 g of the compound of the formula (1) are introduced at 20°-25° C. into 50 ml of oleum (20% of free SO$_3$) and the mixture is stirred for 15 hours at room temperature. The homogeneous solution is then discharged onto 200 g of ice and the mixture is stirred for 1 hour. The crystalline precipitate is filtered off, stirred with 200 ml of acetone for 1 hour, filtered off, washed with acetone and dried in vacuo at 70° C. 11.3 g of the compound of the formula

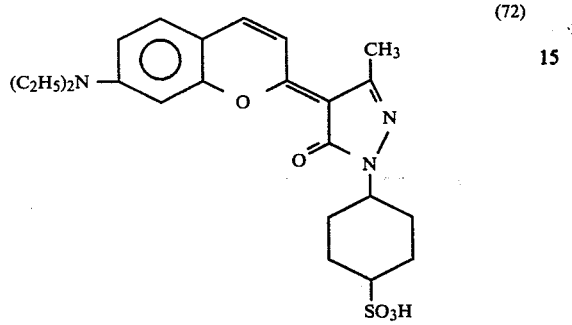

(72)

are obtained in the form of deep red crystals. Dyeings on polyamide fabric have a strongly bluish-tinged scarlet shade which is fast to light and dyeings on wool have a bluish-tinged red shade which is fast to light.

The following acid dyestuffs are prepared in an analogous manner: compounds of the formula

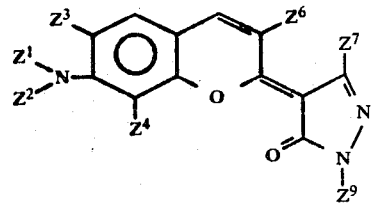

| No. | $Z^1$ | $Z^2$ | $Z^3$ | $Z^4$ | $Z^6$ | $Z^7$ | $Z^9$ | Colour shade (polyamide) |
|---|---|---|---|---|---|---|---|---|
| (73) | C$_2$H$_5$ | C$_2$H$_5$ | H | H | H | CH$_3$ | HO$_3$S—⌬—Cl (3-Cl) | clear bluish-tinged scarlet |
| (74) | HO$_3$S—⌬—CH$_2$ | CH$_3$ | H | H | H | CH$_3$ | Cl$_3$-⌬ (2,4,5-Cl$_3$) | brilliant bluish-tinged scarlet |
| (75) | C$_2$H$_5$ | HO$_3$S—⌬—CH$_2$ | H | H | H | CH$_3$ | Cl$_2$-⌬ (2,4-Cl$_2$) | brilliant bluish-tinged scarlet |
| (76) | HO$_3$S—⌬ | CH$_3$ | H | H | H | CH$_3$ | HO$_3$S—⌬ | bluish-tinged scarlet |
| (77) | n-C$_3$H$_7$ | n-C$_3$H$_7$ | H | H | H | CH$_3$ | CH$_3$—⌬—SO$_3$H | bluish-tinged scarlet |
| (78) | n-C$_4$H$_9$ | n-C$_4$H$_9$ | H | H | H | CH$_3$ | HO$_3$S—⌬ | bluish-tinged scarlet |
| (79) | C$_2$H$_5$ | C$_2$H$_5$ | H | H | CH$_3$ | H | HO$_3$S—⌬ | orange |
| (80) | C$_2$H$_5$ | C$_2$H$_5$ | H | H | H | HO$_3$S—⌬ | Cl$_3$-⌬ (2,4,5-Cl$_3$) | clear bluish-tinged scarlet |
| (81) | HO$_3$S—⌬—CH$_2$ | CH$_3$ | H | H | H | CH$_3$ | CH$_3$ | bluish-tinged scarlet |
| (82) | HO$_3$S—⌬—CH$_2$ | HO$_3$S—⌬—CH$_2$ | H | H | H | CH$_3$ | HO$_3$SO—(CH$_2$)$_2$SO$_2$—⌬ | clear orange |
| (83) | C$_2$H$_5$ | C$_2$H$_5$ | H | H | H | HO$_3$S—⌬ | O$_2$N—⌬ | bluish-tinged scarlet |

-continued

| No. | $Z^1$ | $Z^2$ | $Z^3$ | $Z^4$ | $Z^6$ | $Z^7$ | $Z^9$ | Colour shade (polyamide) |
|---|---|---|---|---|---|---|---|---|
| (84) | $CH_3$ | $CH_3$ | H | H | H | $CH_3$ | $HO_3S-\langle\bigcirc\rangle-$ | bluish-tinged scarlet |
| (85) | $C_2H_5$ | H | $CH_3$ | H | H | $CH_3$ | $HO_3S-\langle\bigcirc\rangle-$ | bluish-tinged scarlet |
| (86) | $C_2H_5$ | H | H | $CH_3$ | H | $CH_3$ | $HO_3S-\langle\bigcirc\rangle-$ | bluish-tinged scarlet |
| (87) | $C_2H_5$ | $C_2H_5$ | H | H | Cl | $CH_3$ | $HO_3S-\langle\bigcirc\rangle-$ | orange |
| (88) | $C_2H_5$ | $C_2H_5$ | H | H | H | $CH_2Cl$ | $HO_3S-\langle\bigcirc\rangle-$ with Cl | clear bluish-tinged scarlet |
| (89) | $C_2H_5$ | $C_2H_5$ | H | H | H | $HO_3S-$ | $Br-\langle\bigcirc\rangle-$ | bluish-tinged scarlet |
| (90) | $C_2H_5$ | $C_2H_5$ | H | H | H | $CH_3$ | $Cl-\langle\bigcirc\rangle-$ with $SO_3H$ | bluish-tinged scarlet |
| (91) | $-(CH_2)_4-$ | | H | H | H | $CH_3$ | $HO_3S-\langle\bigcirc\rangle-$ | bluish-tinged scarlet |
| (92) | $-(CH_2)_2O-(CH_2)_2-$ | | H | H | H | $CH_3$ | $HO_3S-\langle\bigcirc\rangle-$ | bluish-tinged scarlet |
| (93) | $C_2H_5$ | $C_2H_5$ | H | H | H | $\underset{N-C_6H_5}{COCH_3}$ | $HO_3S-\langle\bigcirc\rangle-$ | bluish-tinged red |

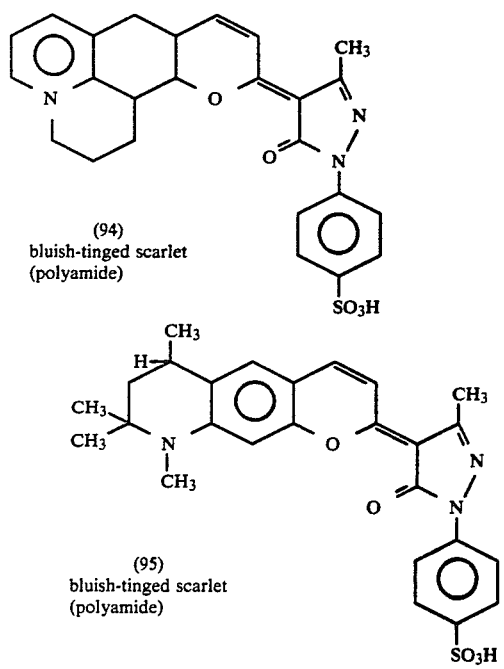

(94) bluish-tinged scarlet (polyamide)

(95) bluish-tinged scarlet (polyamide)

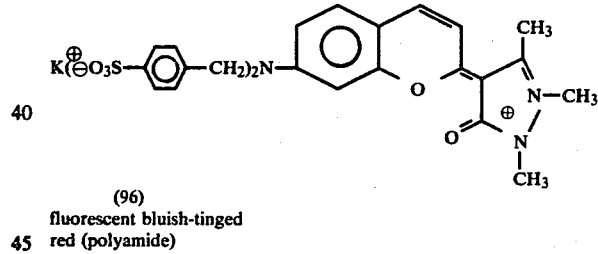

(96) fluorescent bluish-tinged red (polyamide)

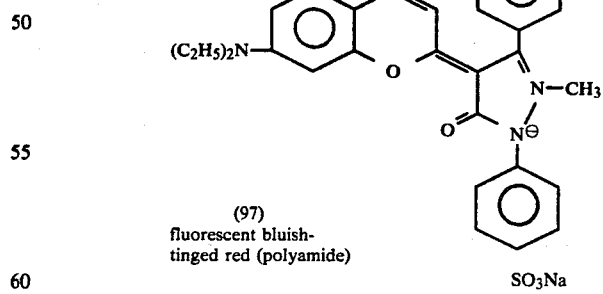

(97) fluorescent bluish-tinged red (polyamide)

EXAMPLE 98

31.3 g of 4-diethylamino-2-hydroxy-2'-carboxy-benzophenone and 21.6 g of 1-phenyl-3-methyl-4-acetyl-pyrazol-5-one in 300 ml of acetic anhydride are heated to the boil under reflux for 2 hours and the mixture is filtered hot. The filtrate is evaporated in vacuo and the residue is recrystallised from ethylene glycol monomethyl ether (140 ml). 23 g of the compound of the formula

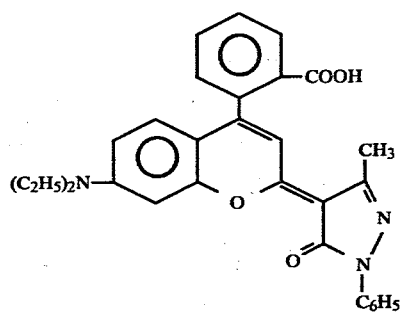

(98)

are obtained in the form of black-violet crystals. On polyester (130° C., closed dyeing apparatus), the dyestuff shows a fluorescent red colour shade with good fastness properties.

If 4-diethylamino-2-hydroxy-2'-carboxy-benzophenone is replaced by an equivalent amount of 4-diethylamino-2-hydroxy-acetophenone, this gives 15 g of the dyestuff of the formula

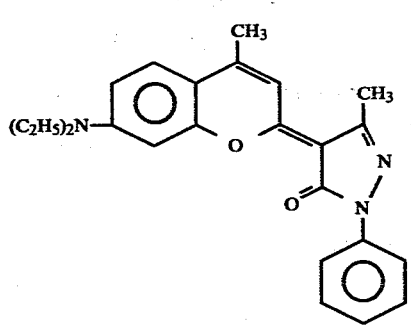

(99)

which dyes polyester yellowish-tinged red. 4-Diethylamino-2-hydroxybenzophenone is also employed in an analogous manner.

EXAMPLE 100

10 g of a compound (98) are suspended in 100 ml of methanol and the suspension is saturated with dry HCl gas at 20°–25° C. and heated to the boil for 20 hours. It is then poured onto a mixture of saturated sodium acetate solution (150 ml) and ice (300 g) and the crystalline precipitate is filtered off, washed with water and dried at 50° C. in vacuo. 10.5 g of the dyestuff of the formula

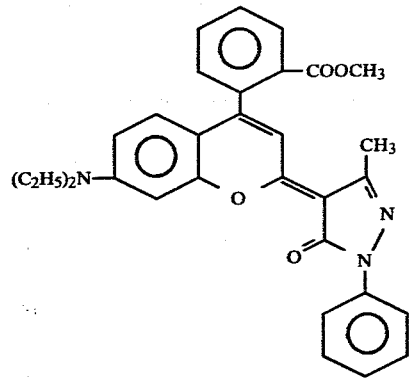

(100)

are obtained in the form of violet crystals. A dyeing on polyester shows a luminous red colour shade with good fastness properties.

In an analogous manner, the ethyl ester is obtained when ethanol is used and the n-butyl ester is obtained when n-butanol is used. These esters display good coloristic properties similar to those of (100).

EXAMPLE 101

120 g of 4-hydroxycoumarin in 600 ml of glacial acetic acid are heated to the boil and 380 ml of phosphorus oxychloride are added dropwise in the course of 60 minutes at the boil. The reaction mixture is heated to the boil under reflux for a further 30 minutes and is cooled and discharged into 4 l of ice-water. The crystalline residue is filtered off, washed with water and dried in vacuo at 50° C. 127 g of 3-acetyl-4-hydroxycoumarin are obtained.

51 g of this compound together with 50 g of 4-diethylaminosalicylaldehyde and 5 ml of piperidine in 500 ml of toluene are heated to the boil under a water separator for 4 hours and the reaction mixture is cooled. The crystalline precipitate is filtered off, washed with toluene, recrystallised from 300 ml of methanol, washed with methanol and dried in vacuo at 50° C. 62 g of the compound of the formula

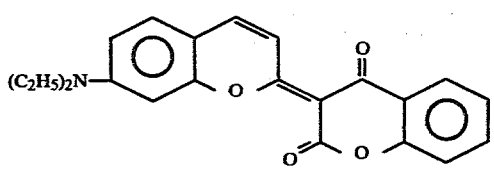

(101)

are obtained in the form of dark red crystals. A dyeing on polyester (130° C.) displays a fluorescent yellowish-tinged scarlet shade.

EXAMPLE 102

358 g of N,N'-dibutylthiourea and 225 g of malonic acid are dissolved in 850 ml of glacial acetic acid, with warming, 190 ml of acetic anhydride are added dropwise at 60° C., with stirring, the mixture is warmed at 70° C. for 2 hours, 100 ml of acetic anhydride are added dropwise, the resulting mixture is warmed at 70° C. for 1 hour, a further 100 ml of acetic anhydride are added dropwise, the resulting mixture is warmed at 90° C. for 3 hours and 70 ml of water are added dropwise at 60°–90° C. The solvent is distilled off in vacuo at 50°–90° C. and the residue is stirred with 1 l of methanol. The crystalline precipitate is filtered off, washed with methanol and dried in vacuo at 40° C. 212 g of N,N'-dibutyl-5-acetyl-thiobarbituric acid are obtained.

60 g of this acid and 40 g of 4-diethylaminosalicylaldehyde in 300 ml of toluene, in the presence of 3 ml of piperidine, are heated to the boil under a water separator for 3 hours. The solution is filtered hot, the filtrate is evaporated in vacuo and the residue is recrystallised from about 200 ml of ethylene glycol monomethyl ether, washed with ethanol and dried in vacuo at 50° C. The dyestuff of the formula

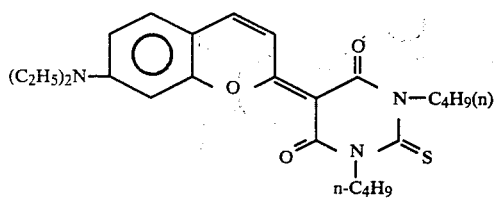

(102)

is obtained in the form of dark red crystals which dye polyester fabric in a fluorescent yellowish-tinged scarlet shade.

If N,N'-dibutylthiourea is replaced by an equivalent amount of N-methylthiourea, this gives N-methyl-5-acetylthiobarbituric acid, which in an analogous manner yields the dyestuff of the formula

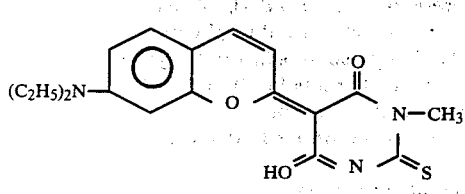

(103)

which is a dark red crystalline powder which dyes polyamide in a fluorescent reddish-tinged orange.

The N-allyl dyestuff prepared in an analogous manner from N-allyl-5-acetylthiourea possesses very similar coloristic properties.

EXAMPLE 104

After adding 10 ml of piperidine, 84 g of dehydroacetic acid and 100 g of 4-diethylaminosalicylaldehyde in 500 ml of toluene are heated to the boil under a water separator for 6 hours. The dyestuff solution is clarified hot using 5 g of bleaching earth (Tonsil) and the filtrate is concentrated to about half its volume. After standing for several days, the crystalline precipitate is filtered off, washed with ice-cold methanol and recrystallised from 120 ml of methanol. 30 g of the compound of the formula

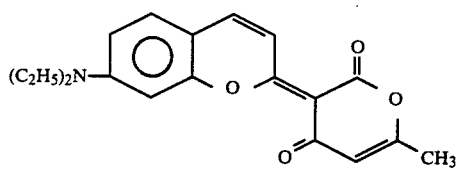

(104)

are obtained in the form of dark red crystals. On polyester, the dyestuff gives a fluorescent reddish-tinged orange shade.

EXAMPLES 105 AND 106

29.5 g of 2-amino-4-dimethylamino-benzaldehyde (prepared according to German Offenlegungsschrift (German Published Specification) No. 2,363,459) and 50 g of 1,3-diphenyl-4-acetyl-pyrazol-5-one and 3 ml of piperidine in 300 ml of xylene are heated to the boil under a water separator for 2 hours and the reaction mixture is then cooled. The crystalline precipitate is filtered off, washed with ethanol, recrystallised from 350 ml of dimethylformamide, washed with ethanol and dried in vacuo at 60° C. 52 g of the compound of the formula

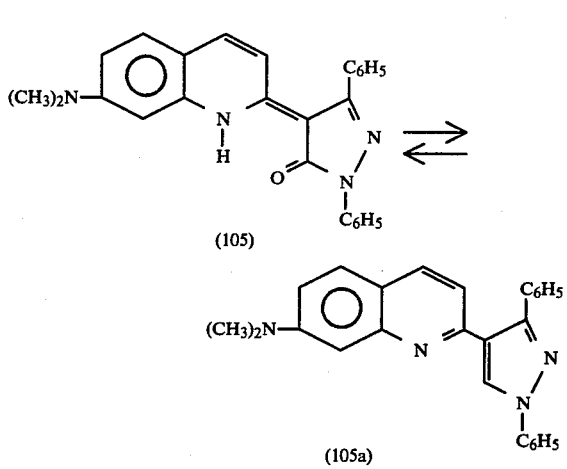

(105)

(105a)

are obtained. This displays a yellowish colour shade on polyester.

8 g of this substance are dissolved at room temperature in 60 ml of oleum (20% SO₃) and after 16 hours the solution is discharged onto ice. The crystalline precipitate is filtered off, stirred with acetone, filtered off again, washed with acetone and dried in vacuo at 50° C. 8 g of the compound of the formula

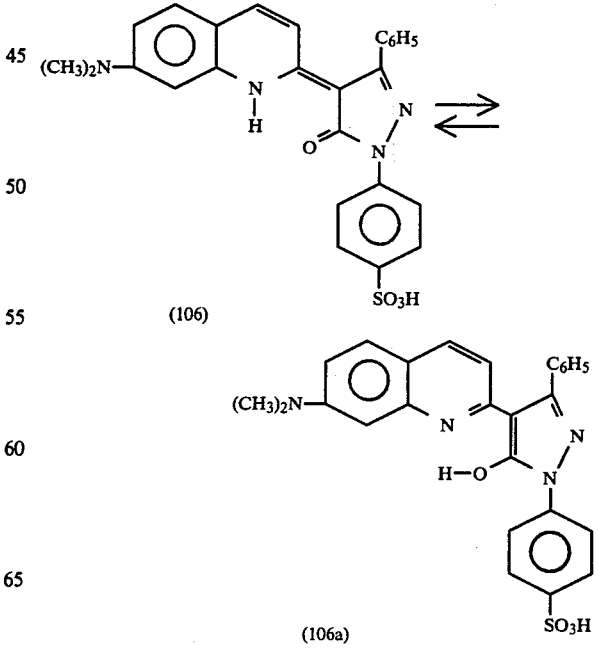

(106)

(106a)

are obtained. This displays a brilliant greenish-tinged yellow colour shade on polyamide.

I claim:

1. A dyestuff of the formula

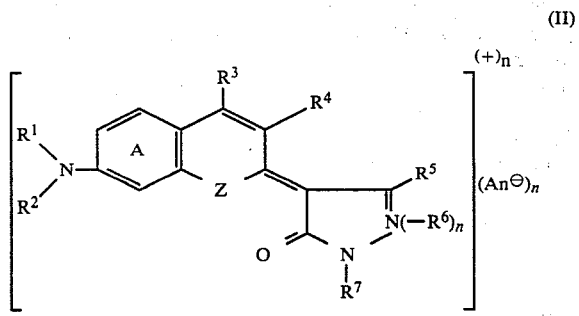

(II)

wherein
- $R^1$ represents hydrogen, alkyl, alkenyl, cycloalkyl, aralkyl, aryl or a 2-membered or 3-membered alkylene radical linked to the adjacent ortho-position of the ring A,
- $R^2$ represents hydrogen, alkyl, alkenyl, aralkyl or a 2-membered or 3-membered alkylene radical linked to the adjacent ortho-position of the ring A,
- $R^3$ represents hydrogen, alkyl, aralkyl, aryl, alkoxy, halogen, cyano, carboxyl, alkoxycarbonyl, alkylsulphonyl or arylsulphonyl,
- $R^4$ represents hydrogen, alkyl, aryl, halogen, hydroxyl, alkoxy, nitro, cyano, carboxyl, alkoxycarbonyl, formyl, carbamoyl, ureido, amidino, amidinium, alkylsulphonyl, arylsulphonyl, sulpho, pyrazol-1-yl, 4-chloropyrazol-1-yl, tetrazol-1-yl, or 1,2,3-triazol-1-yl, 1,2,3-triazol-2-yl, 1,2,4-triazol-1-yl or benzo-s-triazol-2-yl, the nitrogen atoms of any of the triazoles optionally being quaternished by $C_1$-$C_4$-alkyl or benzyl,
- Z represents oxygen or sulphur,
- $R^5$ represents hydrogen, alkyl, aralkyl, aryl, chlorine, bromine, carboxyl, alkoxycarbonyl, carbamoyl, cyano, hydroxyl, alkoxy, acyloxy or a radical of the formula —$N(R^8R^9)$,
- $R^6$ represents alkyl, alkenyl or aralkyl,
- n represents 0 or 1,
- $R^7$ represents alkyl, aralkyl or aryl,
- $R^8$ represents hydrogen, alkyl, aralkyl, cycloalkyl, aryl, pyridyl, thienyl or sulpholan-3-yl,
- $R^9$ represents an acyl radical, and
- $An^-$ represents an anion, and wherein the cyclic and acyclic radicals can carry substituents selected from the group consisting of $C_1$-$C_4$-alkyl, OH, $C_1$-$C_4$ alkoxy, halogen, sulpho, CN and $NO_2$.

2. A dyestuff according to claim 1, of the formula

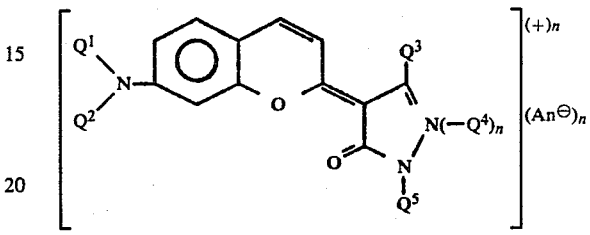

wherein
- $Q^1$ represents methyl, ethyl, n-propyl, n-butyl, benzyl, sulphobenzyl, β-phenylethyl or sulpho-β-phenylethyl,
- $Q^2$ has one of the meanings of $Q^1$,
- $Q^3$ represents methyl,
- $Q^4$ represents methyl, ethyl, n-propyl, n-butyl, β-hydroxyethyl, β-hydroxy-n-propyl, allyl or benzyl,
- $Q^5$ represents methyl, ethyl, phenyl, chlorophenyl, dichlorophenyl, trichlorophenyl, bromophenyl, sulphophenyl, sulphochlorophenyl or nitrophenyl,
- n represents the number 0 or 1 and
- $An^\ominus$ represents an anion.

3. A dyestuff according to claim 2, characterised in that
- n represents the number 1,
- $Q^1$ and $Q^2$ represent methyl, ethyl, benzyl or sulphobenzyl,
- $Q^3$ represents methyl,
- $Q^4$ represents methyl, ethyl, β-hydroxyethyl or β-hydroxy-n-propyl and
- $Q^5$ represents methyl, ethyl, phenyl or sulphophenyl.

* * * * *